United States Patent
Kim et al.

(10) Patent No.: US 8,507,625 B2
(45) Date of Patent: Aug. 13, 2013

(54) MICHAEL ACCEPTOR HAVING MULTIPLE HYDROXYL GROUPS, AND MICHAEL ADDITION PRODUCT DERIVED THEREFROM

(75) Inventors: Young Chul Kim, Daejeon (KR); Byung Hoon Lee, Gyeongsangbuk-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 12/876,935

(22) Filed: Sep. 7, 2010

(65) Prior Publication Data
US 2011/0251338 A1    Oct. 13, 2011

(30) Foreign Application Priority Data
Apr. 8, 2010  (KR) .................. 10-2010-0032257

(51) Int. Cl.
| | |
|---|---|
| *C08F 222/14* | (2006.01) |
| *C08F 222/20* | (2006.01) |
| *C08F 290/04* | (2006.01) |
| *C07C 69/734* | (2006.01) |
| *C08F 290/06* | (2006.01) |
| *C07C 69/716* | (2006.01) |

(52) U.S. Cl.
CPC ........... *C08F 290/067* (2013.01); *C07C 69/716* (2013.01)
USPC ........... 526/301; 526/320; 560/209; 560/220; 560/224

(58) Field of Classification Search
USPC ................... 560/205–224; 526/301, 320
See application file for complete search history.

(56) References Cited

U.S. PATENT DOCUMENTS

| | | | |
|---|---|---|---|
| 5,243,069 A * | 9/1993 | Emmons ................. | 560/224 |
| 5,565,525 A | 10/1996 | Morimoto et al. | |
| 5,945,489 A | 8/1999 | Moy et al. | |
| 6,025,410 A | 2/2000 | Moy et al. | |

(Continued)

FOREIGN PATENT DOCUMENTS

| | | |
|---|---|---|
| JP | 2000-072832 A | 3/2000 |
| JP | 2006-111880 A | 4/2006 |
| KR | 10-0903209 B | 6/2009 |

OTHER PUBLICATIONS

Machine translated English equivalent of KR 10-0903209 (22 pages, Sep. 2009).*
Office action issued by Korean Patent Office for priority Korean application 10-2010-0032257 dated Nov. 23, 2011.

(Continued)

*Primary Examiner* — Ling Choi
*Assistant Examiner* — Brieann R Fink
(74) *Attorney, Agent, or Firm* — Frommer Lawrence & Haug LLP; Ronald R. Santucci (57) ABSTRACT

Provided is a Michael addition product prepared from a multifunctional acryl monomer having multiple hydroxyl groups allowing introduction of acryl functional groups, as a Michael acceptor, and a Michael donor. The Michael addition product is a novel multifunctional compound having an oligomer and a photoinitiator moiety in the molecule. Since it can be cured under a standard UV curing condition without having to add a photoinitiator, it is reduced to air pollution or health problem. Therefore the superior physical properties were obtained by cured coatings without surface tackiness. In addition, its hydroxyl groups allow, through isocyanate bonding or introduction of acryl groups, 3-dimensional crosslinking and molecular and compositional design for improving expandability, friction, and reactivity and hydrophilicity for self-adhesion, hardness of cured film, or the like. Consequently, a very useful, multifunctional or water-dispersible coating composition may be prepared.

19 Claims, 8 Drawing Sheets

(56) References Cited

U.S. PATENT DOCUMENTS

| | | |
|---|---|---|
| 7,514,528 B2 * | 4/2009 | Kauffman et al. ............ 528/392 |
| 2005/0261388 A1 | 11/2005 | Gould et al. |
| 2007/0004815 A1 | 1/2007 | Narayan-Sarathy et al. |
| 2009/0030106 A1 | 1/2009 | Jacobine et al. |

OTHER PUBLICATIONS

Kim, Young Chul et al.: "Synthesis and Characterization of UV-curable Aliphatic Epoxy Acrylate", *Journal of Adhesion and Interface*, vol. 10, No. 4, 2009, pp. 191-198, in Korean but includes English abstract.

* cited by examiner

MICHAEL ACCEPTOR HAVING MULTIPLE HYDROXYL GROUPS, AND MICHAEL ADDITION PRODUCT DERIVED THEREFROM

CROSS-REFERENCE TO RELATED APPLICATIONS

This application claims priority under 35 U.S.C. §119 to Korean Patent Application No. 10-2010-0032257, filed on Apr. 8, 2010, in the Korean Intellectual Property Office, the disclosure of which is incorporated herein by reference in its entirety.

TECHNICAL FIELD

The following disclosure relates to a Michael acceptor having multiple hydroxyl groups and a Michael addition product derived therefrom. More particularly, the following disclosure relates to a Michael acceptor having multiple hydroxyl groups allowing introduction of functional groups to provide mechanical properties such as expandability, friction, etc., as well as various other properties such as reactivity and hydrophilicity for self-adhesion as desired, and a Michael addition product derived therefrom. The Michael acceptor and its addition product may be used as a UV- and electron beam-curable self-photoinitiator as well as an oligomer. Accordingly, they may be widely applicable in information and communications, semiconductors, electric/electronic fields, micropattern printing, wood coating and others.

BACKGROUND

UV-curable resin, when exposed to UV, forms oligomers and monomers having UV-reactive groups. The resulting polymer is an insoluble material having a highly dense network as well as good heat resistance and chemical stability and superior optical and mechanical properties. Since the UV curing is accomplished in a relatively short time, it consumes less energy and provides good productivity thus being widely used in various fields. In addition, it has many other advantages that it is environment friendly, by not using any solvent, providing convenience by requiring only a small workplace, etc.

In general, the UV-reactive (meth)acrylate groups of monomers and oligomers may be crosslinked by a free radical chain mechanism by a photoinitiator. When exposed to UV or electron beam (EB), they turn to free radicals by the photoinitiator at a lower activation energy.

The photoinitiator has a disadvantage that it raises a safety issue. In fact, during or after the preparation of the photoinitiator, there is produced volatile, low-molecular-weight decomposition product, which can be easily absorbed through the respiratory organs or skin of workers, thereby affecting their health conditions.

Several solutions to this problem have been introduced. For example, there was an attempt to solve the problem by using a (meth)acrylate resin having a self-photoinitiating ability.

U.S. Pat. No. 5,565,525 (Nippon Paint, Japan, 1994) discloses a Michael addition product which is a UV-curable resin having four acryl functional groups prepared from a β-dicarbonyl Michael donor and a multifunctional acrylate Michael acceptor. It is prepared via a Michael addition reaction in the presence of an epoxide residue and a quaternary salt as catalyst. Although crosslinking is achieved without a photoinitiator, surface properties may not be good because of steric hindrance and improper acryl crosslinking density.

U.S. Pat. Appl. Pub. No. 2005-0261388 (Ashland, 2005) discloses a liquid, uncrosslinked, UV-curable Michael addition product having four acryl functional groups prepared from a multifunctional acrylate Michael acceptor and an optically active β-dicarbonyl Michael donor substituted with a photoinitiator. When exposed to UV, the resulting oligomer facilitates addition polymerization of the acryl groups through self-photoinitiation and improvement of optical activity by the introduced photoinitiator. Although viscosity is low and curing reactivity is superior, surface properties are not greatly improved because of improper acryl crosslinking density.

The self-photoinitiating (meth)acrylate oligomer prepared by Michael addition does not provide a desired effect when considering the additional preparation processes and cost. It is because the Michael acceptor has low acrylic functionality. Accordingly, it may be still required to add a volatile, low-molecular-weight multifunctional monomer to improve crosslinkability of the composition, which may negatively affect the reactivity and final property, as well as a photoinitiator.

Thus, various technical developments are underway to allow preparation of a photocurable (meth)acrylate resin in a safe and environment-friendly way without using an additional photoinitiator. Especially, techniques of preparing a (meth)acrylate oligomer having a built-in photoinitiator using no photoinitiator are presented.

In 1997, Ashland developed and patented a self-photoinitiating resin having 8 acryl functional groups from a multifunctional acrylate Michael acceptor and a β-dicarbonyl diacetoacetate Michael donor (U.S. Pat. Nos. 5,945,489 and 6,025,410). In 2009, Chokwang Paint developed a photocurable (meth)acrylate resin having four acryl functional groups through addition of a hydroxyacrylate Michael acceptor to a β-dicarbonyl donor followed by urethane bonding, which is capable of photocuring in the absence of a photoinitiator (Korean Patent No. 10-0903209).

U.S. Pat. Appl. Pub. No. 0004815 A1 (Ashland, 2007) discloses a self-photoinitiating multifunctional urethane acrylate having four acryl functional groups prepared from a Michael addition reaction with a β-dicarbonyl Michael donor, wherein an amine-based synergist is used to provide improved photocuring reactivity.

However, in order to improve effective performance, a Michael addition product having more acryl functional groups is required.

SUMMARY

The inventors of the present invention have been making efforts to develop a Michael addition product having more acryl functional groups than existing Michael addition products, and, as a result, completed the present invention.

An embodiment of the present invention is directed to providing a Michael acceptor having multiple hydroxyl groups and a method for preparing the same. Another embodiment of the present invention is directed to providing a Michael addition product derived from the Michael acceptor and a method for preparing the same. Still another embodiment of the present invention is directed to providing a coating film including a cured, crosslinked residue of the Michael addition product.

In one aspect, the present invention provides a Michael acceptor having multiple hydroxyl groups. The Michael acceptor is represented by Chemical Formula 1:

(1)

wherein X is $C_1$-$C_6$ alkylene or $C_3$-$C_{10}$ cycloalkylene; $R_1$ and $R_2$, which may be identical to or different from each other, are hydrogen or $C_1$-$C_6$ alkyl; and n is an integer from 0 to 10.

In another aspect, the present invention provides a Michael addition product derived from the Michael acceptor, which is represented by Chemical Formula 2 or Chemical Formula 3:

wherein X is $C_1$-$C_6$ alkylene or $C_3$-$C_{10}$ cycloalkylene; $R_1$, $R_1'$, $R_2$, and $R_2'$, which may be identical to or different from one another, are hydrogen or $C_1$-$C_6$ alkyl; n is an integer from 0 to 10; $R_3$ is $C_1$-$C_{12}$ alkyl, benzyl, benzoyl, acryl or amide; and $R_4$ is independently hydrogen or multifunctional isocyanate.

In still another aspect, the present invention provides a coating film including a cured, crosslinked residue of the Michael addition product.

The Michael acceptor of the present invention has multiple hydroxyl groups allowing introduction of functional groups. A crosslinkage of 3 or higher dimension may be formed by introducing an adequate binder. Further, mechanical properties such as expandability, friction, etc., as well as various other properties such as reactivity for self-adhesion, hydrophilicity, etc., may be provided. In addition, the Michael acceptor of the present invention may further have a urethane acrylate moiety, which is formed through bonding with isocyanate, in addition to the epoxy acrylate moiety. As such, molecular design is possible by varying the proportion and the characteristics of the cured resin may be varied as desired.

Since the Michael addition product derived from the Michael acceptor has a high acryl content, it has superior curability and hardness of the cured film. Further, since it has a photoinitiating group, it may be cured under a standard UV curing condition without adhesion, without having to use an additional photoinitiator or photosensitizer. In addition, energy consumption required for uniform dispersion of the photoinitiator may be saved. Further, since no decomposition product is formed after the curing, desired performance may be attained without air pollution or health problem.

Other features and aspects will be apparent from the following detailed description, the drawings, and the claims.

BRIEF DESCRIPTION OF THE DRAWINGS

The above and other objects, features and advantages of the present invention will become apparent from the following description of preferred embodiments given in conjunction with the accompanying drawings, in which.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Hereunder is given a more detailed description of the present invention.

The present invention provides a Michael acceptor having multiple hydroxyl groups, which is represented by Chemical Formula 1.

The Michael acceptor represented by Chemical Formula 1 may be a Michael acceptor represented by Chemical Formula 8 or 9:

Hence, health problem or environmental pollution may be minimized.

Preferably, the Michael acceptor represented by Chemical Formula 1 may be synthesized by reacting an acrylate having a carboxylic acid group represented by Chemical Formula 4 or 5 with an epoxy resin represented by Chemical Formula 6 in a reactor by heating:

wherein X is alkylene, $R_1$ is hydrogen or $C_1$-$C_6$ alkyl, Y is cycloalkylene, phenyl, ethylene or caprolactone, and n is an integer of 2 or 3; and wherein X is $C_1$-$C_6$ alkylene or $C_3$-$C_{10}$ cycloalkylene, and n is an integer of from 0 to 10.

Specifically, the acrylate having a carboxyl group represented by Chemical Formula 4 or 5 may be 2-carboxyethyl acrylate, 2-carboxypropyl acrylate, 2-acryloyloxyethyl phthalate, 2-acryloyloxyethyl hexahydrophthalate, 2-acry- Since the Michael acceptor of the present invention has multiple hydroxyl groups unlike the existing Michael acceptors, it may be designed to exhibit adequate properties. And, since the Michael addition product prepared from addition of the Michael acceptor has an initiating group capable of initiating photoreaction, it is unnecessary to additionally use a photoinitiator. As a result, formation of volatile, low-molecular-weight substances, which are easily absorbed through skin, due to decomposition by heat or light may be avoided.

loyloxypropyl phthalate, ethylene oxide (EO) added succinic acid acrylate, ω-carboxypolycaprolactone acid acrylate or a methacrylate thereof.

And, preferably, the epoxy resin represented by Chemical Formula 6 may be one or more selected from the group consisting of 1,4-butanediol diglycidyl ether, 1,4-cyclohexanedimethanol diglycidyl ether, diglycidyl 1,2-cyclohexanedicarboxylate, glycerol diglycidyl ether, neopentyl glycol diglycidyl ether, pentaerythritol diglycidyl ether, ethylene glycol diglycidyl ether, propylene glycol diglycidyl ether, 1,6-hexanediol diglycidyl ether, trimethylolpropane diglycidyl ether and diethylene glycol diglycidyl ether.

The reaction may be promoted by a base catalyst such as an onium salt or a tertiary amine. Examples of the catalyst include triethylamine, benzyldimethylamine, methyl triethylammonium chloride, benzyltrimethylammonium bromide, benzyltrimethylammonium iodide, triphenylphosphine, triphenylstibine, chromium octanoate, zirconium octanoate, etc. Preferably, the catalyst is used in an amount of 1 to 5 wt% based on the weight of the glycidyl compound.

Since the Michael acceptor represented by Chemical Formula 1, 8 or 9 has much more hydroxyl groups than existing Michael acceptors, it may be designed to exhibit adequate properties.

The present invention also provides a Michael addition product derived from the Michael acceptor represented by Chemical Formula 1.

The Michael addition product may be represented by Chemical Formula 2 or 3:

group consisting of toluene-2,4-diisocyanate, toluene-2,6-diisocyanate, 1,5-naphthalene diisocyanate, 4-methoxy-1,3-phenylene diisocyanate, 4-chloro-1,3-phenylene diisocyanate, 2,4-dimethyl-1,3-phenylene diisocyanate, 4,4-diisocyanate diphenyl ether, benzidine diisocyanate, dibenzyl -4,4'-diisocyanate and methylene-bis(4-phenylisocyanate)-1,3-phenylene diisocyanate.

All or part of the multifunctional isocyanate may have a multifunctional acryl group. It may be prepared by reacting the Michael addition product having an isocyanate group with hydroxyl acrylate at 50 to 80° C. for 1 to 5 hours. Since the Michael addition product has a multifunctional acrylate moiety, which is formed through bonding with isocyanate, in addition to the epoxy acrylate moiety of existing Michael addition products, it may be designed to exhibit adequate properties.

Specifically, the multifunctional isocyanate may be represented by Chemical Formula 7:

wherein X is $C_1$-$C_6$ alkylene or $C_3$-$C_{10}$ cycloalkylene; $R_1$, $R_1'$, $R_2$, and $R_2'$, which may be identical to or different from one another, are hydrogen or $C_1$-$C_6$ alkyl; n is an integer from 0 to 10; $R_3$ is $C_1$-$C_{12}$ alkyl, benzyl, benzoyl, acryl or amide; and $R_4$ is independently hydrogen or multifunctional isocyanate.

In Chemical Formula 3, the multifunctional isocyanate is a structure or a functional group derived from an aliphatic diisocyanate, an aromatic diisocyanate or a combination thereof.

The aliphatic diisocyanate may be one or more selected from the group consisting of hexamethylene diisocyanate, 4,4-dicyclohexylmethane diisocyanate, 1,4-tetramethylene diisocyanate, 1,10-decamethylene diisocyanate, isophorone diisocyanate and 1,4-cyclohexane diisocyanate, and the aromatic diisocyanate may be one or more selected from the The Michael addition product represented by Chemical Formula 2 is a UV-curable, bifunctional acrylate Michael addition product having hydroxyl groups. It has multiple pendant hydroxyl groups allowing 3-dimensional crosslinking and molecular and compositional design for improving expandability, friction, and reactivity and hydrophilicity for self-adhesion or the like. Further, it may be modified by substituting the hydroxyl groups with other functional groups.

Since the Michael addition product represented by Chemical Formula 2 or 3 has an initiating group capable of initiating photoreaction, it is unnecessary to additionally use a photoinitiator. As a result, formation of volatile, low-molecular-weight substances, which are easily absorbed through skin, due to decomposition by heat or light may be avoided. Hence, health problem or environmental pollution may be minimized.

The Michael addition product represented by Chemical Formula 2 may be synthesized from a Michael acceptor and a Michael donor.

In the present invention, the Michael donor refers to a compound acting as an electron donor in Michael addition reaction wherein a compound having activated methylene is added to an α,β-unsaturated carbonyl compound or an α,β-unsaturated nitrile compound.

Specifically, the Michael addition product is synthesized by reacting the Michael acceptor represented by Chemical Formula 1 with a Michael donor in a reactor at 60 to 100° C. for 3 to 5 hours. Preferably, the Michael donor is a β-dicarbonyl Michael donor.

The β-dicarbonyl Michael donor may be one or more selected from the group consisting of a β-keto ester, a β-diketone, a β-keto amide and a β-keto anilide.

Alternatively, the β-dicarbonyl Michael donor may be one or more selected from the group consisting of acetoacetate, 2,4-pentanedione, acetoacetanilide and acetoacetamide.

Alternatively, the β-dicarbonyl Michael donor may be one or more selected from the group consisting of methyl acetoacetate, ethyl acetoacetate, t-butyl acetoacetate, allyl acetoacetate, 2-ethylhexyl acetoacetate, lauryl acetoacetate and 2-acetoacetoxyethyl methacrylate (AAEM) having two functional groups per molecule.

Alternatively, the β-dicarbonyl Michael donor may be one or more selected from the group consisting of 1,4-butanediol diacetoacetate, 1,6-hexanediol diacetoacetate, neopentyl glycol diacetoacetate, cyclohexane dimethanol diacetoacetate and ethoxylated bisphenol A diacetoacetate having four functional groups per molecule.

Alternatively, the β-dicarbonyl Michael donor may be one or more selected from the group consisting of trimethylol propane triacetoacetate, glycerol triacetoacetate, poly caprolactone triacetoacetate, ethoxylated or propoxylated trimethylol propane triacetoacetate and ethoxylated or propoxylated glycerol triacetoacetate having six functional groups per molecule.

Alternatively, the β-dicarbonyl Michael donor may be one or more selected from the group consisting of pentaerythritol tetraacetoacetate and ethoxylated or propoxylated pentaerythritol tetraacetoacetate having eight functional groups per molecule.

Alternatively, the β-dicarbonyl Michael donor may be one or more selected from the group consisting of malonic acid ester, o-acetoacetaniside, o-acetoacetatoluidide, N,N-dimethylacetoacetamide, methyl cyanoacetate, ethyl cyanoacetate and butyl cyanoacetate.

That is to say, various Michael donors may be selected depending on the desired physical property or reactivity.

The Michael addition reaction between the Michael acceptor and the β-dicarbonyl Michael donor may be promoted by a strong base. An example of a base which is sufficiently strong and is easily solubilized in a monomer mixture is diazabicycloundecene (DBU). In addition, a cyclic amidine such as diazabicyclononene (DBN) and guanidine is also suitable to catalyze the reaction. Typically, also a Group I metal alkoxide base such as potassium t-butoxide is adequate to promote the reaction. A quaternary hydroxide and alkoxide, e.g., tetrabutylammonium hydroxide and benzyltrimethylammonium methoxide, may also be used as a base catalyst to promote the Michael addition. As a result, an organophilic alkoxide strong base may be generated in-situ from the reaction between a halide anion (e.g., quaternary halide) and the epoxide moiety.

The Michael addition product represented by Chemical Formula 3 may be prepared from the Michael addition product represented by Chemical Formula 2 by substituting the hydrogen atoms of the hydroxyl groups with multifunctional isocyanate. The substitution may be carried out by adding the Michael addition product represented by Chemical Formula 2, the multifunctional isocyanate and a multifunctional acryl monomer to a reactor and then performing reaction at 30 to 60° C. for 2 to 4 hours.

The Michael addition product of the present invention may also be modified to a primary or secondary amine by adding an amine synergist so as to block oxygen in the air. As a result, photoreactivity may be enhanced. As an example of such modification, a primary or secondary amine may be mixed with an uncured Michael addition product. Specifically, after adding diethanolamine to the Michael addition product represented by Chemical Formula 2 or 3, followed by stirring at room temperature, the resulting product may be exposed to UV. Typical examples of the primary amine include ethanolamine, methyl-1,6-hexanediamine, 3-aminopropyltrimethoxysilane, diaminopropane, benzylamine, triethylenetetraamine, isophoronediamine and a mixture thereof. Typical examples of the secondary amine include dimethylamine, dibutylamine, diethanolamine, piperidine, morpholine and a mixture thereof. In case a liquid Michael addition product is modified with a primary or secondary amine, it may be accomplished simply by reacting the modified amine with the liquid, uncured Michael addition product.

The present invention further provides a coating film comprising a cured, crosslinked residue of the Michael addition product. Because the Michael addition product of the present invention has a built-in photoinitiating group, the coating film may be prepared by exposing it to UV, without necessitating the use of an additional photoinitiator or photosensitizer.

EXAMPLES

The examples and experiments will now be described. The following examples and experiments are for illustrative purposes only and not intended to limit the scope of this disclosure.

The Michael addition product of the present invention was coated on a surface to demonstrate its UV photopolymerization performance. The resin composition was coated on a glass substrate by the draw-down technique to a thickness of 10 μm or smaller. Then, UV was irradiated at 500 mJ/cm$^2$ for adhesion-free curing.

Example 1

Synthesis of Michael Acceptor Having Hydroxyl Groups

2-Carboxyethyl acrylate (28.826 g, 0.2 mol), glycerol diglycidyl ether (20.433 g, 0.1 mol) and triethylamine (2 wt % based on glycerol diglycidyl ether) were sequentially added to a 4-bulb glass flask reactor equipped with a reflux condenser, a nitrogen inlet, a stirrer and a heater. After raising temperature to 60° C., reaction was carried out for 4 hours without using a polymerization inhibitor. Then, after cooling to room temperature and transferring to a separatory funnel, 5% HCl aqueous solution was added to neutralize the remaining catalyst and the salt was removed. Then, after washing 2 to 3 times with distilled water, a Michael acceptor having hydroxyl groups was obtained at 50° C. under reduced pressure as transparent liquid. The Michael acceptor was separated and purified to obtain a main product with the byproduct removed.

Figure 1:
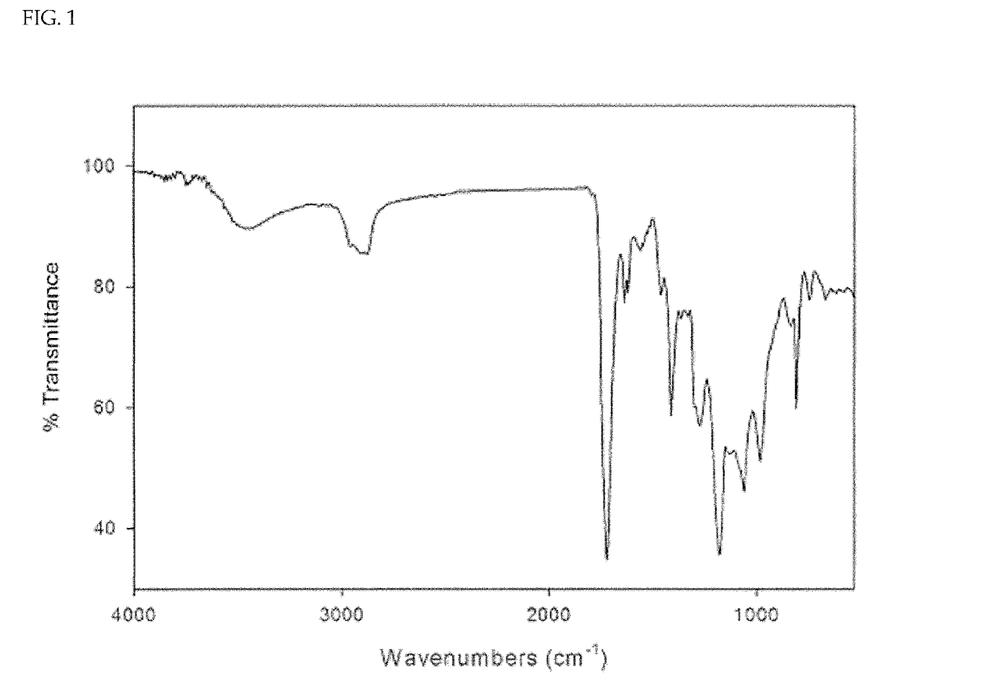
FIG. 1 shows an FT-IR spectrum of a Michael acceptor synthesized according to the present invention in Example 1.
Figure 2:
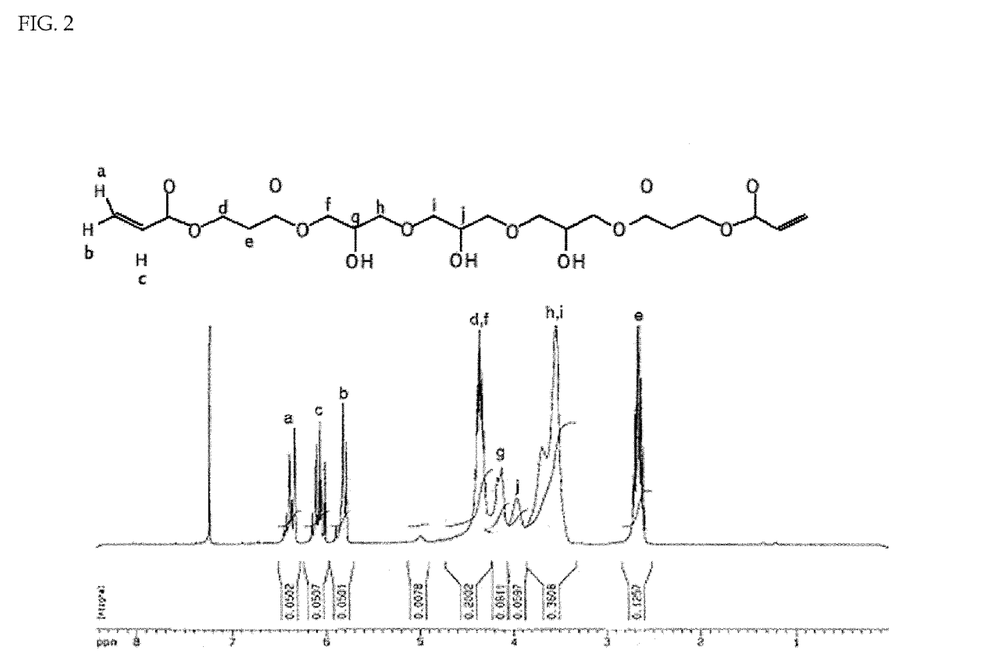
FIG. 2 shows a $^1$H-NMR spectrum of a Michael acceptor synthesized according to the present invention in Example 1.
Figure 3:
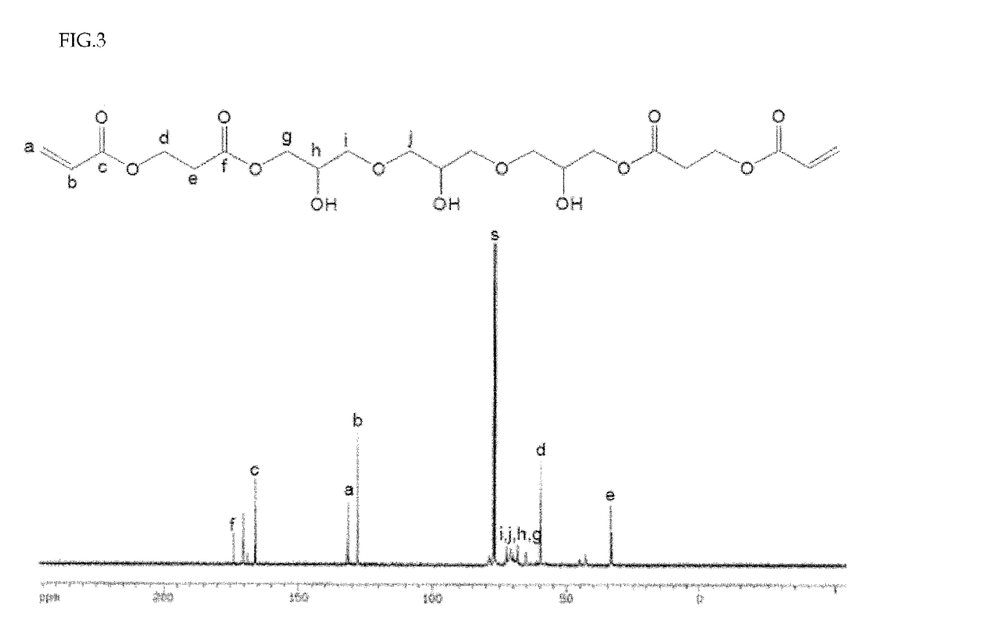
FIG. 3 shows a $^{13}$C-NMR spectrum of a Michael acceptor synthesized according to the present invention in Example 1.
Figure 4:
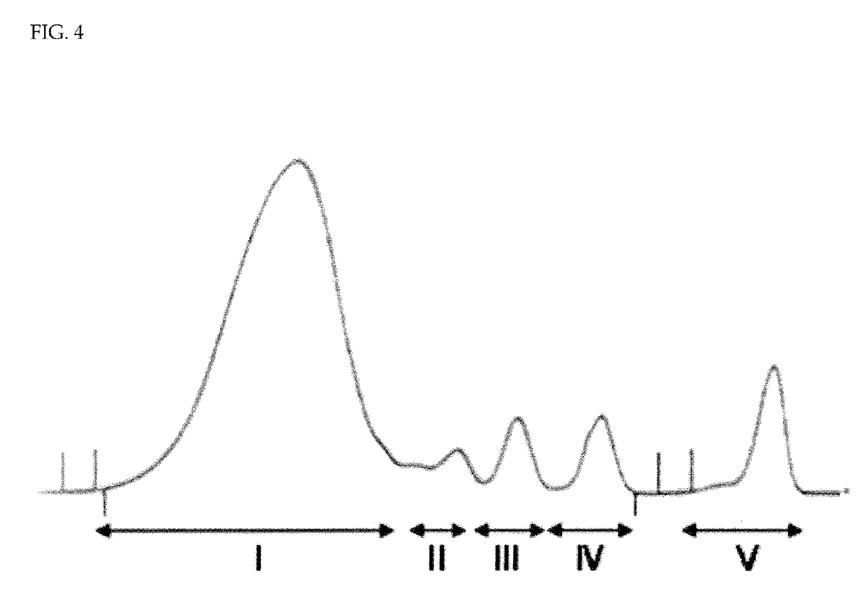
FIG. 4 shows a prep-LC result of a Michael acceptor synthesized according to the present invention in Example 1.

FIG. 1 shows an FT-IR spectrum of the Michael acceptor prepared in Example 1. FIGS. 2, 3 and 4 respectively show a $^1$H-NMR spectrum, a $^{13}$C-NMR spectrum and a prep-LC result.

prep-LC (yield): 83%.

IR (KBr, cm$^{-1}$): 3421 (—OH), 2919 (aliphatic C—H), 1727 (C=O), 1635 & 1618 (C=C), 1186 & 1122 (C—O—C), 984 (=CH$_2$ twisting vibration).

$^1$H-NMR (CDCl$_3$, 300 MHz), δ (ppm): 5.80-6.33 (m, 3H, —CH=CH$_2$), 4.13 & 4.31-4.41 (m, 5H, —CH$_2$CHOHCH$_2$OOCCH$_2$CH$_2$—), 3.98 (m, 1H, —CH$_2$CHOHCH$_2$—), 3.55 & 3.70 (m, 4H, —CH$_2$OCH$_2$—), 2.61-2.72 (m, 2H, —CH$_2$COO—).

$^{13}$C-NMR (CDCl$_3$, 75 MHz), δ (ppm): 173.63 (—CH$_2$COO—), 165.99 (CH$_2$=CHCOO—), 131.20 (CH$_2$=CH—), 127.97 (CH$_2$=CH—), 65.14-73.05 (—COOCH$_2$CHOHCH$_2$OCH$_2$CHOH—), 59.83 (CH$_2$=CHCOOCH$_2$—), 33.18 (CH$_2$=CHCOOCH$_2$CH$_2$—).

Example 2

Synthesis of Michael Acceptor Having Hydroxyl Groups

Figure 5:
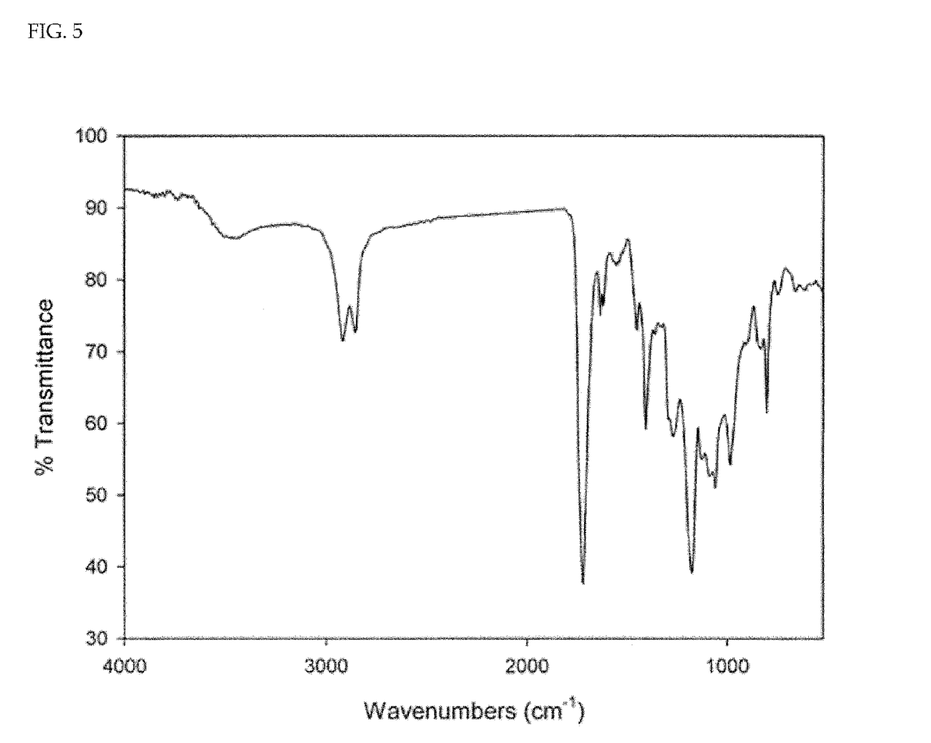
FIG. 5 shows an FT-IR spectrum of a Michael acceptor synthesized according to the present invention in Example 2.
Figure 6:
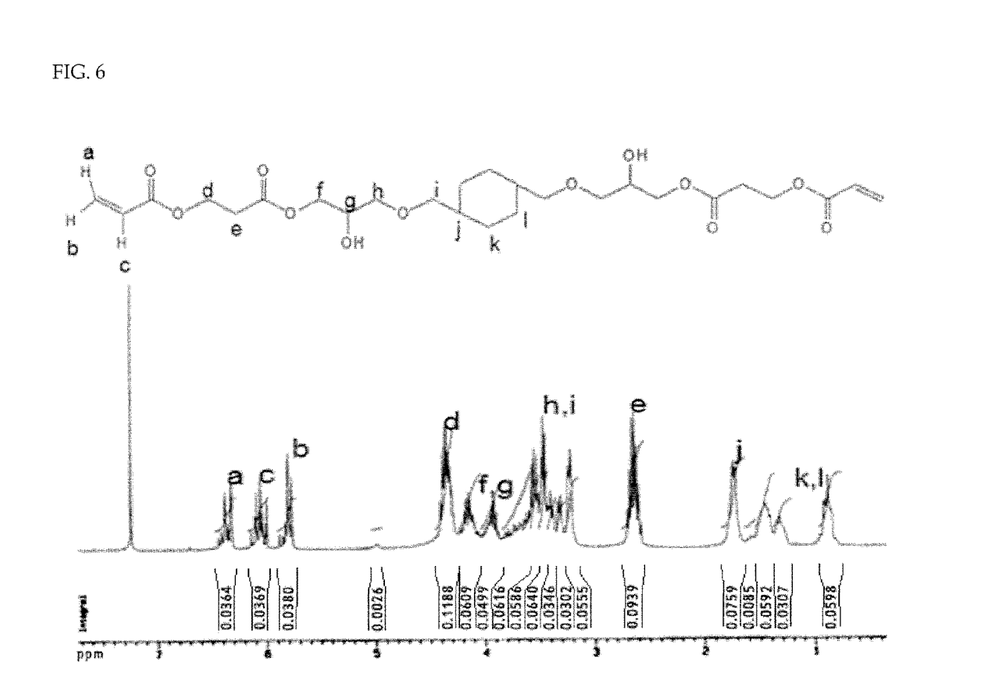
FIG. 6 shows a $^1$H-NMR spectrum of a Michael acceptor synthesized according to the present invention in Example 2.
Figure 7:
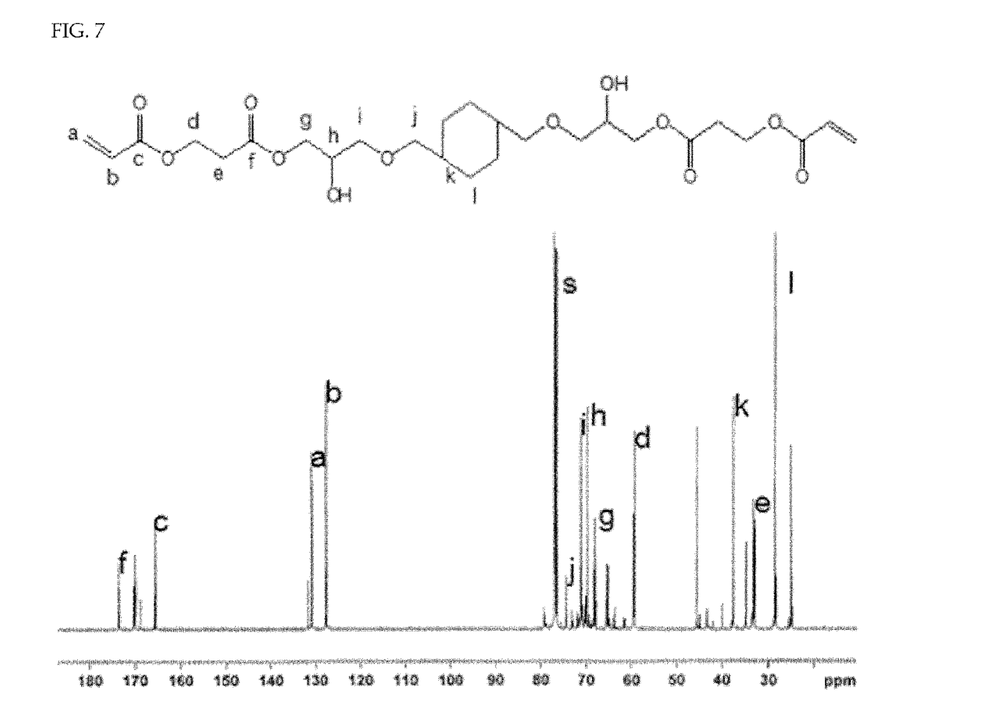
FIG. 7 shows a $^{13}$C-NMR spectrum of a Michael acceptor synthesized according to the present invention in Example 2.
Figure 8:
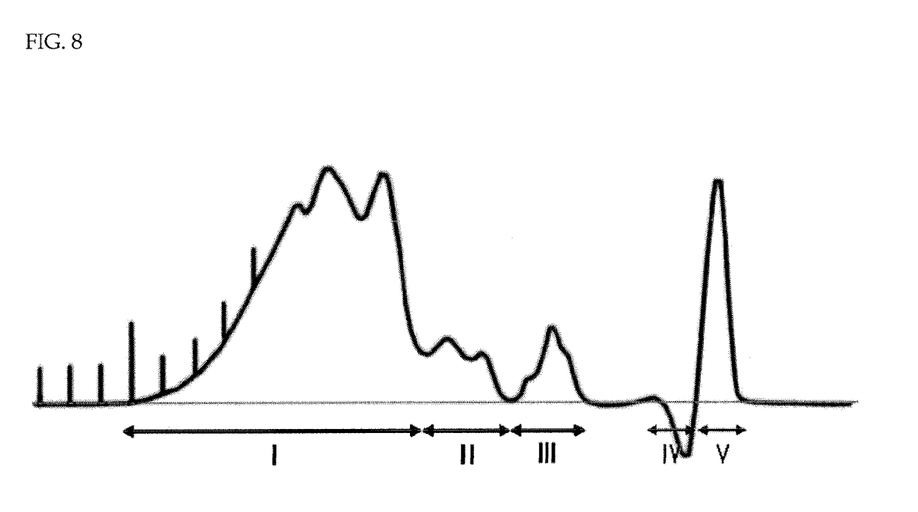
FIG. 8 shows a prep-LC result of a Michael acceptor synthesized according to the present invention in Example 2.

2-Carboxyethyl acrylate (28.826 g, 0.2 mol), 1,4-cyclohexanedimethanol diglycidyl ether (25.634 g, 0.1 mol) and triethylamine (2 wt % based on 1,4-cyclohexanedimethanol diglycidyl ether) were sequentially added to a 4-bulb glass flask reactor equipped with a reflux condenser, a nitrogen inlet, a stirrer and a heater. After raising temperature to 60° C., reaction was carried out for 4 hours without using a polymerization inhibitor. Then, after cooling to room temperature and transferring to a separatory funnel, 5% HCl aqueous solution was added to neutralize the remaining catalyst and the salt was removed. Then, after washing 2 to 3 times with distilled water, a Michael acceptor having hydroxyl groups was obtained at 50° C. under reduced pressure as transparent liquid. The Michael acceptor was separated and purified to obtain a main product with the byproduct removed. FIG. 5 shows an FT-IR spectrum of the Michael acceptor prepared in Example 2. FIGS. 6, 7 and 8 respectively show a $^1$H-NMR spectrum, a $^{13}$C-NMR spectrum and a prep-LC result.

prep-LC (yield): 73%.

IR (KBr, cm$^{-1}$): 3421 (—OH), 2919 (aliphatic C—H), 1727 (C=O), 1635 & 1618 (C=C), 1186 & 1122 (C—O—C), 984 (=CH$_2$ twisting vibration).

$^1$H-NMR (CDCl$_3$, 300 MHz), δ (ppm): 5.80-6.33 (m, 3H, —CH=CH$_2$), 4.32-4.40 (m, 2H, —COOCH$_2$CH$_2$COO—), 3.91-4.17 (m, 3H, —COOCH$_2$CHOHCH$_2$—), 3.22-3.57 (m, 4H, —CHOHCH$_2$OCH$_2$—), 2.60-2.68 (m, 2H, —CH$_2$COO—), 0.85-2.60 (m, 5H, —CHCH$_2$CH$_2$CH-(cyclohexane)).

$^{13}$C-NMR (CDCl$_3$, 75 MHz), δ (ppm): 173.54 (—CH$_2$COO—), 165.54 (CH$_2$=CHCOO—), 130.93 (CH$_2$=CH—), 127.54 (CH$_2$=CH—), 68.13-74.42 (—COOCH$_2$CHOHCH$_2$OCH$_2$CH—), 59.41 (CH$_2$=CHCOOCH$_2$—), 37.53 (cyclohexane, —CHCH$_2$—), 33.00 (—CH$_2$COO—), 28.72 (cyclohexane, —CHCH$_2$CH$_2$CH—).

Example 3

Synthesis of Michael Addition Product Having Built-in Photoinitiating Group The Michael acceptor having hydroxyl groups prepared in Example 1 (20.19 g, 0.04 mol), ethyl acetoacetate (2.64 g, 0.02 mol), glycidyl methacrylate (0.46 g, 2 wt %) and tetrabutylammonium bromide (0.12 g, 0.5 wt %) were added to a 4-bulb glass flask reactor equipped with a reflux condenser, a nitrogen inlet, a stirrer and a heater. The mixture was mixed while stirring adequately using a mechanical stirrer. Then, the reactor was heated to 80° C. at a rate of 1° C./min and then kept at the temperature for 3 hours. 3 hours later, the resulting resin was taken out of the reactor and then cooled to obtain a Michael addition product having a built-in photoinitiating group.

The Michael addition product was coated on a glass substrate to a thickness of 10 μm, and then adhesion-freely cured by exposing to UV at 500 mJ/cm². The cured coating was smooth, glossy and soft.

IR (KBr, cm$^{-1}$): 3421 (—OH), 2919 (aliphatic C—H), 1727 (C=O), 1635 & 1618 (C=C), 1186 & 1122 (C—O—C), 984 (=CH$_2$ twisting vibration).

$^{13}$C-NMR (CDCl$_3$, 75 MHz), δ (ppm): 208.7 (CH$_3$C=OC—), 173.63 (—CH$_2$COO—), 172.7 (—CCOOCH$_2$CH$_3$), 165.99 (CH$_2$=CHCOO—), 131.20 (CH$_2$=CH—), 127.97 (CH$_2$=CH—), 65.14~73.05 (—COOCH$_2$CHOHCH$_2$OCH$_2$CHOH—), 61.6 (—COOCH$_2$CH$_3$), 59.83 (—COOCH$_2$CH$_2$COO—), 33.18 (—COOCH$_2$CH$_2$COO—), 26.9☐28.4 (—OOCCH$_2$CH$_2$CCH$_2$CH$_2$COO—), 25.9 (CH$_3$C=OC—), 14.1 (—COOCH$_2$CH$_3$).

Example 4

Synthesis of Michael Addition Product Having Built-in Photoinitiating Group The Michael acceptor having hydroxyl groups prepared in Example 2 (21.78 g, 0.04 mol), ethyl acetoacetate (2.64 g, 0.02 mol), glycidyl methacrylate (0.50 g, 2 wt %) and tetrabutylammonium bromide (0.12 g, 0.5 wt %) were added to a 4-bulb glass flask reactor equipped with a reflux condenser, a nitrogen inlet, a stirrer and a heater. The mixture was mixed while stirring adequately using a mechanical stirrer. Then, the reactor was heated to 80° C. at a rate of 1° C./min and then kept at the temperature for 3 hours. 3 hours later, the resulting resin was taken out of the reactor and then cooled to obtain a Michael addition product having a built-in photoinitiating group.

The Michael addition product was coated on a glass substrate to a thickness of 10 μm, and then adhesion-freely cured by exposing to UV at 500 mJ/cm². The cured coating was smooth, glossy and soft.

IR (KBr, cm$^{-1}$): 3421 (—OH), 2919 (aliphatic C—H), 1727 (C=O), 1635 & 1618 (C=C), 1186 & 1122 (C—O—C), 984 (=CH$_2$ twisting vibration).

$^{13}$C-NMR (CDCl$_3$, 75 MHz), δ (ppm): 208.7 (CH$_3$C=OC—), 173.54 (—CH$_2$COO—), 172.7 (—CCOOCH$_2$CH$_3$), 165.54 (CH$_2$=CHCOO—), 130.93 (CH$_2$=CH—), 127.54 (CH$_2$=CH—), 68.13☐74.42 (—COOCH$_2$CHOHCH$_2$OCH$_2$CH—), 61.6 (—COOCH$_2$CH$_3$), 59.41 (—COOCH$_2$CH$_2$COO—), 37.53 (cyclohexane, —CHCH$_2$—), 33.00 (—CH$_2$COO—), 28.72 (cyclohexane, —CHCH$_2$CH$_2$CH—), 25.9 (CH$_3$C=OC—), 14.1 (—COOCH$_2$CH$_3$).

Example 5

Synthesis of Michael Addition Product Having Built-in Photoinitiating Group

The Michael addition product prepared in Example 3 (30 g, 0.027 mol), acetone (50 g) and dibutyltin dilaurate (0.1 g) were added to a 4-bulb glass flask reactor equipped with a reflux condenser, a nitrogen inlet, a stirrer and a heater. The mixture was mixed while stirring adequately using a mechanical stirrer. Then, the reactor was heated to 45° C. over 20 minutes. While maintaining the temperature at 45° C., isophorone diisocyanate (35.88 g, 0.161 mol) was added dropwise over 1 hour. Then, the temperature was raised to 60° C. over 3 hours.

The reaction was monitored by FT-IR. The temperature of the reaction mixture was lowered to 45-50° C. when the intensity at 3400 cm$^{-1}$ (—OH band) became a minimum value. Then, after adding pentaerythritol triacrylate (48.02 g, 0.161 mol), the reaction mixture was further stirred and heated. To prevent gelation, phenothiazine (0.01 g) was added.

The reaction was monitored by FT-IR. Acetone was removed by vacuum distillation at 60° C. and 100 mmHg when the intensity at 2300 cm$^{-1}$ (—NCO band) became a minimum value. A urethane acrylate type Michael addition product was obtained.

The Michael addition product was coated on a glass substrate to a thickness of 10 μm, and then adhesion-freely cured by exposing to UV at 500 mJ/cm$^2$. The cured coating was smooth, glossy and hard.

Example 6

Synthesis of Michael Addition Product Having Built-in Photoinitiating Group

The Michael addition product prepared in Example 4 (30 g, 0.025 mol), acetone (50 g) and dibutyltin dilaurate (0.1 g) were added to a 4-bulb glass flask reactor equipped with a reflux condenser, a nitrogen inlet, a stirrer and a heater. The mixture was mixed while stirring adequately using a mechanical stirrer. Then, the reactor was heated to 45° C. over 20 minutes. While maintaining the temperature at 45° C., isophorone diisocyanate (32.81 g, 0.148 mol) was added dropwise over 1 hour. Then, the temperature was raised to 60° C. over 3 hours.

The reaction was monitored by FT-IR. The temperature of the reaction mixture was lowered to 45-50° C. when the intensity at 3400 cm$^{-1}$ (—OH band) became a minimum value. Then, after adding pentaerythritol triacrylate (44.15 g, 0.148 mol), the reaction mixture was further stirred and heated. To prevent gelation, phenothiazine (0.01 g) was added.

The reaction was monitored by FT-IR. Acetone was removed by vacuum distillation at 60° C. and 100 mmHg when the intensity at 2300 cm$^{-1}$ (—NCO band) became a minimum value. A urethane acrylate type Michael addition product was obtained.

The Michael addition product was coated on a glass substrate to a thickness of 10 μm, and then adhesion-freely cured by exposing to UV at 500 mJ/cm$^2$. The cured coating was smooth, glossy and hard.

While the present invention has been described with respect to the specific embodiments, it will be apparent to those skilled in the art that various changes and modifications may be made without departing from the spirit and scope of the invention as defined in the following claims.

What is claimed is:

1. A Michael addition product represented by Chemical Formula 2:

wherein X is $C_1$-$C_6$ alkylene or $C_3$-$C_{10}$ cycloalkylene; $R_1$, $R_1'$, $R_2$ and $R_2'$, which may be identical to or different from one another, are hydrogen or $C_1$-$C_6$ alkyl; n is an integer from 1 to 10; and $R_3$ is $C_1$-$C_{12}$ alkyl, benzyl, benzoyl, acryl or amide.

2. A Michael addition product represented by Chemical Formula 3:

wherein X is $C_1$-$C_6$ alkylene or $C_3$-$C_{10}$ cycloalkylene; $R_1$, $R_1'$, $R_2$, and $R_2'$, which may be identical to or different from one another, are hydrogen or $C_1$-$C_6$ alkyl; n is an integer from 1 to 10; $R_3$ is $C_1$-$C_{12}$ alkyl, benzyl, benzoyl, acryl or amide; and $R_4$ is a residue of a multifunctional isocyanate.

3. The Michael addition product according to claim 2, wherein the residue of the multifunctional isocyanate is a structure or a functional group derived from an aliphatic diisocyanate, an aromatic diisocyanate or a combination thereof.

4. The Michael addition product according to claim 3, wherein the aliphatic diisocyanate is one or more selected from the group consisting of hexamethylene diisocyanate, 4,4-dicyclohexylmethane diisocyanate, 1,4-tetramethylene diisocyanate, 1,10-decamethylene diisocyanate, isophorone diisocyanate and 1,4-cyclohexane diisocyanate.

5. The Michael addition product according to claim 3, wherein the aromatic diisocyanate is one or more selected from the group consisting of toluene-2,4-diisocyanate, toluene-2,6-diisocyanate, 1,5-naphthalene diisocyanate, 4-methoxy-1,3-phenylene diisocyanate, 4-chloro-1,3-phenylene diisocyanate, 2,4-dimethyl-1,3-phenylene diisocyanate, 4,4-diisocyanate diphenyl ether, benzidine diisocyanate, dibenzyl-4,4'-diisocyanate and methylene-bis(4-phenylisocyanate)-1,3-phenylene diisocyanate.

6. The Michael addition product according to claim 2, wherein all or part of the residue of the multifunctional isocyanate has a multifunctional acryl group.

7. The Michael addition product according to claim 2, wherein all or part of the residue of the multifunctional isocyanate is represented by Chemical Formula 7:

(7)

8. A method for preparing a Michael addition product represented by Chemical Formula 2 comprising reacting a β-dicarbonyl Michael donor with a Michael acceptor represented by Chemical Formula 1:

(1)

wherein X is $C_1$-$C_6$ alkylene or $C_3$-$C_{10}$ cycloalkylene; $R_1$, $R_1'$, $R_2$ and $R_2'$, which may be identical to or different from one another, are hydrogen or $C_1$-$C_6$ alkyl; n is an integer from 1 to 10; and $R_3$ is $C_1$-$C_{12}$ alkyl, benzyl, benzoyl, acryl or amide.

9. The method for preparing a Michael addition product according to claim 8, wherein the β-dicarbonyl Michael donor is one or more selected from the group consisting of a β-keto ester, a β-diketone, a β-keto amide and a β-keto anilide.

10. The method for preparing a Michael addition product according to claim 8, wherein the β-dicarbonyl Michael donor is one or more selected from the group consisting of acetoacetate, 2,4-pentanedione, acetoacetanilide and acetoacetamide.

11. The method for preparing a Michael addition product according to claim 8, wherein the β-dicarbonyl Michael donor is one or more selected from the group consisting of methyl acetoacetate, ethyl acetoacetate, t-butyl acetoacetate, allyl acetoacetate, 2-ethylhexyl acetoacetate, lauryl acetoacetate and 2-acetoacetoxyethyl methacrylate (AAEM) having two functional groups per molecule.

12. The method for preparing a Michael addition product according to claim 8, wherein the β-dicarbonyl Michael donor is one or more selected from the group consisting of 1,4-butanediol diacetoacetate, 1,6-hexanediol diacetoacetate, neopentyl glycol diacetoacetate, cyclohexane dimethanol diacetoacetate and ethoxylated bisphenol A diacetoacetate having four functional groups per molecule.

13. The method for preparing a Michael addition product according to claim 8, wherein the β-dicarbonyl Michael donor is one or more selected from the group consisting of trimethylol propane triacetoacetate, glycerol triacetoacetate, poly caprolactone triacetoacetate, ethoxylated or propoxylated trimethylol propane triacetoacetate and ethoxylated or propoxylated glycerol triacetoacetate having six functional groups per molecule.

14. The method for preparing a Michael addition product according to claim 8, wherein the β-dicarbonyl Michael donor is one or more selected from the group consisting of pentaerythritol tetraacetoacetate and ethoxylated or propoxylated pentaerythritol tetraacetoacetate having eight functional groups per molecule.

15. The method for preparing a Michael addition product according to claim 8, wherein the β-dicarbonyl Michael donor is one or more selected from the group consisting of malonic acid ester, o-acetoacetaniside, o-acetoacetatoluidide, N,N-dimethylacetoacetamide, methyl cyanoacetate, ethyl cyanoacetate and butyl cyanoacetate.

16. The method for preparing a Michael addition product according to claim 8, wherein the Michael addition reaction between the Michael acceptor and the β-dicarbonyl Michael donor is promoted by diazabicycloundecene (DBU), diazabicyclononene (DBN), guanidine or potassium t-butoxide.

17. A method for modifying a Michael addition product comprising modifying the Michael addition product of claim 2 by mixing it with a primary or secondary amine.

18. A coating film comprising a cured, crosslinked residue of the Michael addition product according to claim 2.

19. The coating film according to claim 18, wherein the Michael addition product is cured by exposing it to UV.

* * * * *